US008697000B2

(12) United States Patent
Reese et al.

(10) Patent No.: US 8,697,000 B2
(45) Date of Patent: Apr. 15, 2014

(54) APPARATUS AND METHOD FOR STERILIZATION

(75) Inventors: William Reese, Gilbert, AZ (US); John Krug, Orange, CA (US)

(73) Assignee: Hewit Medical, LLC, Tempe, AZ (US)

( * ) Notice: Subject to any disclaimer, the term of this patent is extended or adjusted under 35 U.S.C. 154(b) by 495 days.

(21) Appl. No.: 12/722,459

(22) Filed: Mar. 11, 2010

(65) Prior Publication Data

US 2011/0223060 A1    Sep. 15, 2011

(51) Int. Cl.
   *A61L 2/00*    (2006.01)
   *A61L 9/00*    (2006.01)

(52) U.S. Cl.
   USPC .......................................... 422/294; 422/292

(58) Field of Classification Search
   USPC ................................ 422/292, 294, 28, 29, 33
   See application file for complete search history.

(56) References Cited

U.S. PATENT DOCUMENTS

| | | | | | |
|---|---|---|---|---|---|
| 4,119,414 | A | * | 10/1978 | Smaling | 95/287 |
| 4,951,666 | A | * | 8/1990 | Inman et al. | 607/114 |
| 5,356,426 | A | * | 10/1994 | Delk et al. | 607/112 |
| 5,640,977 | A | * | 6/1997 | Leahy et al. | 128/897 |
| 6,116,723 | A | * | 9/2000 | Childers | 347/85 |
| 6,375,048 | B1 | * | 4/2002 | van der Meer et al. | 222/396 |
| 6,723,056 | B1 | * | 4/2004 | Alving et al. | 600/543 |
| 2003/0089739 | A1 | * | 5/2003 | O'Connor et al. | 222/145.5 |
| 2004/0216802 | A1 | * | 11/2004 | O'Connor et al. | 141/1 |
| 2007/0036711 | A1 | * | 2/2007 | Fisher et al. | 423/648.1 |
| 2008/0105711 | A1 | * | 5/2008 | Kirimli et al. | 222/209 |
| 2009/0283541 | A1 | * | 11/2009 | Compton et al. | 222/105 |
| 2013/0011896 | A1 | * | 1/2013 | Strehler | 435/167 |

OTHER PUBLICATIONS

U.S. Appl. No. 61/286,323, filed Dec. 14, 2009.*

* cited by examiner

*Primary Examiner* — Regina M Yoo
(74) *Attorney, Agent, or Firm* — Wright Law Group, PLLC; Mark F. Wright

(57) ABSTRACT

The present invention provides an apparatus and method for disinfecting a target area of a patient's body, such as an arm, leg or a chest, in a pre-surgical environment. The apparatus and method disclosed herein further provides for maintaining the target area of the patient's body in an aseptic condition while transporting the patient to and into the surgery room. The most preferred embodiments of the present invention contemplate the use of one or more sterile layers (e.g., sterilized bags or the like) that are used to enclose the target area of the patient's body coupled with a sterile substance delivery mechanism that disinfects the target area and also maintains the target area in an aseptic condition. The most preferred embodiments of the present invention comprise a single-layer disposable garment or an inner bag nested inside an outer bag with a sterilization material being introduced into the inner bag, thereby disinfecting the target area. Once the patient has been transported into the operating room, the healthcare professional can remove the disposable garment or the outer bag, and then expose the target area for the selected procedure. Since the target area has been disinfected and also maintained in an aseptic condition, the healthcare professional can immediately begin to perform a selected procedure on the patient without having to spend additional time in the operating room to disinfect the target area of the patient's body that will undergo the selected procedure.

13 Claims, 10 Drawing Sheets

APPARATUS AND METHOD FOR STERILIZATION

BACKGROUND OF THE INVENTION

1. Technical Field

The present invention relates generally to medical procedures and relates more specifically to a sterilization procedure that may be performed in a pre-operative environment using a unique garment or dressing.

2. Background Art

Healthcare professionals recognize the importance of preparing patients for medical procedures by disinfecting the target area where the procedure is to be performed with a topical aseptic preparation, such as chlorhexidine gluconate or rubbing alcohol. During surgery, in order to perform certain procedures, healthcare professionals are frequently required to penetrate or open up one or more areas of a patient's body, for example, the skin of the chest area. If the target area of the patient's body has not been properly sanitized, breaking through the surface layer of the patient's body may increase the risk that the patient will become infected. For example, if healthcare professionals opened up a patient's chest area for open heart surgery but neglected to aseptically prepare the chest area prior to making incisions, then any bacteria, viruses, or other organisms that were originally located on or near the surface of the skin and in proximity to the incision or entry point may migrate to and enter the open wound, thereby infecting the patient.

Typically, a surgical patient is prepared for surgery by administering a 3 to 10 minute scrubbing of the target surgical area with a soap solution, followed by painting the target area with a water-soluble antiseptic solution in the operating room or surgical theater. This pre-surgical preparation of the target area has improved with the use of antiseptics that require only surficial contact with the skin. Delivery devices have also been developed to apply these antiseptic solutions by sponging, brushing, spraying, and/or painting the target area once the patient arrives in the operating room. The current methods of sterilization, however, do not address, among other things, the increased risk of transferring infectious disease between patients, healthcare professionals and others that may occur prior to the surgical preparation of the target area in the operating room.

The current pre-surgical disinfectant methods all present certain drawbacks, which may be broadly categorized into four specific areas of concern: increasing the time that the patient spends in the operating room; increasing the length of time that patient is under anesthesia; increasing the risk of injury to operating room professionals while moving and/or holding the patient in order to sterilize the target area; and increasing the risk of transferring an infection to or from the patient during the pre-operative period.

Using the current methods for preparing patients for surgery, precious time that could be spent performing the operation may be spent on disinfecting the surgical surface area of the patient's body, which is usually an area of skin. Additionally, even if the sterilization of the target area is accomplished in a pre-operative environment, the target area of the patient's body may be exposed to the air or other contaminants and can become unsterile. If the patient's clothing or the target area has become unsterile during the course of transportation, there is a risk that the target area of the patient's body could be subject to infection once the procedure begins.

Another risk posed by current methods is they generally increase the time that a patient is under anesthesia, which is less than ideal since extended exposure to anesthesia may pose some risk for the patient. Further, the common practice of performing the surgical preparation in the operating room using current methods typically requires operating room personnel to lift, hold, and/or move patients since the patient has usually been anesthetized and can no longer control the movement of their body. This may cause physical stress on the personnel performing the pre-operative sterilization procedure and may require additional time from surgeons, anesthesiologists, surgical nurses, and technicians. Accordingly, without improvements in the current process for preparing a patient for surgery, the costs and risks associated with disinfecting the target area of the patient's body associated with pre-operative sterilization will continue to be measurably higher than desired.

BRIEF SUMMARY OF THE INVENTION

The present invention provides an apparatus and method for disinfecting a target area of a patient's body, such as an arm, leg or a chest, in a pre-surgical environment. The apparatus and method disclosed herein further provides for maintaining the target area of the patient's body in an aseptic condition while transporting the patient to and into the surgery room. The most preferred embodiments of the present invention contemplate the use of one or more sterile layers (e.g., sterilized bags or the like) that are used to enclose the target area of the patient's body coupled with a sterile substance delivery mechanism that disinfects the target area and also maintains the target area in an aseptic condition. The most preferred embodiments of the present invention comprise a single-layer disposable garment or an inner bag nested inside an outer bag with a sterilization material being introduced into the inner bag, thereby disinfecting the target area. Once the patient has been transported into the operating room, the healthcare professional can remove the disposable garment or the outer bag, and then expose the target area for the selected procedure. Since the target area has been disinfected and also maintained in an aseptic condition, the healthcare professional can immediately begin to perform a selected procedure on the patient without having to spend additional time in the operating room to disinfect the target area of the patient's body that will undergo the selected procedure.

BRIEF DESCRIPTION OF THE FIGURES

The preferred embodiments of the present invention will hereinafter be described in conjunction with the appended drawings, wherein like designations denote like elements, and.

DETAILED DESCRIPTION OF THE INVENTION

Figure 1:
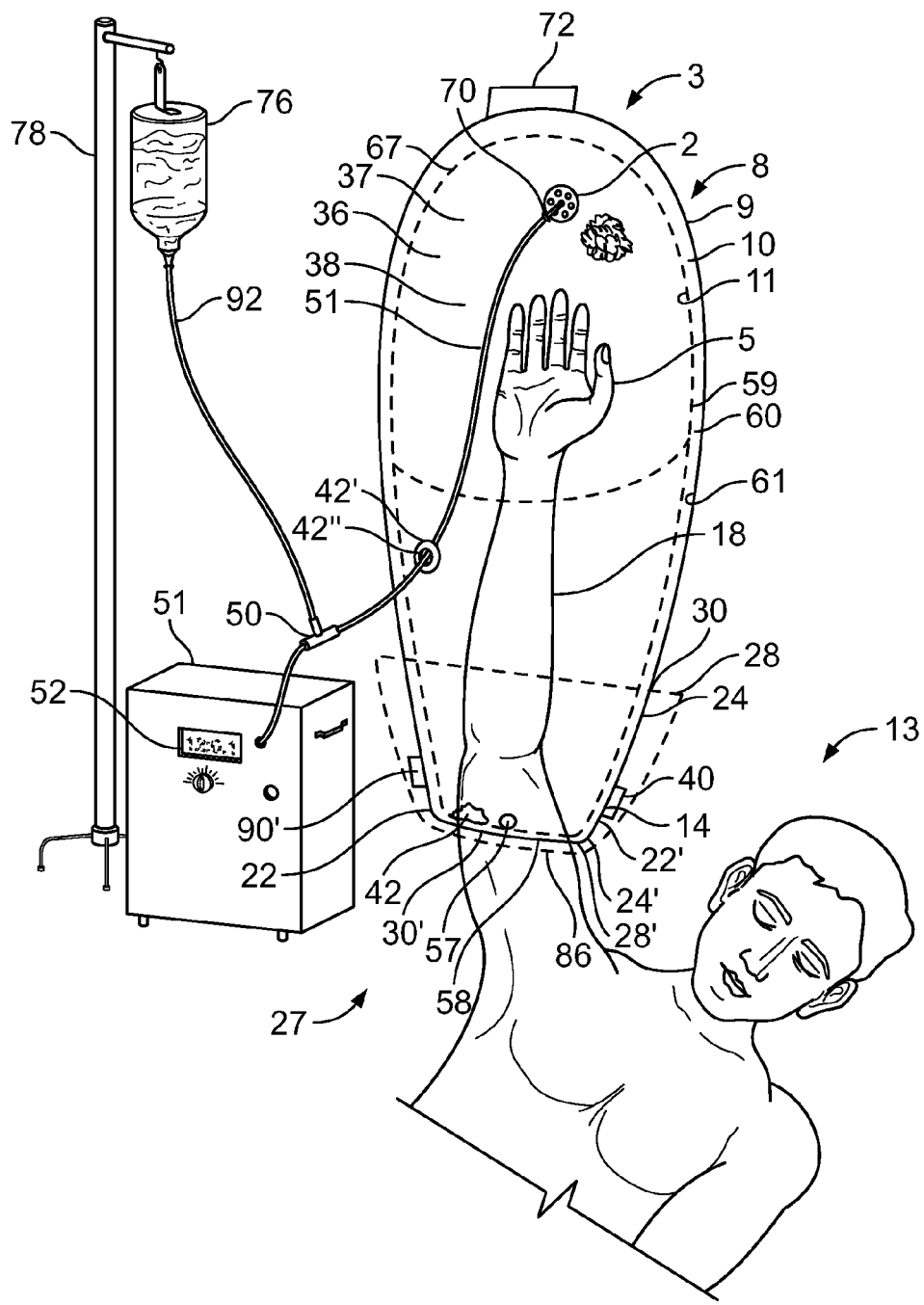
FIG. 1 is a perspective view of the apparatus according deployed in conjunction with a patient in accordance with a preferred exemplary embodiment of the present invention.

Referring now to FIG. 1, an apparatus 27 in accordance with a preferred embodiment of the present invention comprises: an inner bag 10; an outer bag 8; and a delivery mechanism 51. The delivery mechanism 51 is selectively configured to deliver one or more sterile substances 70 to the interior space 38 of inner bag 10. Sterile substances comprise aseptics and disinfectants. Inner bag 10 comprises an interior surface 11, an annular space 37, an exterior surface 12, and an interior space 38.

Interior space 38 comprises an annular space 37 within inner bag 10 and interior surface of inner bag 10. Outer bag 8 comprises an interior surface 61, an annular space 59, an exterior surface 9, and an interior space 60. Interior space 60 of outer bag 8 comprises annular space 59 and interior surface 11.

Sterile substance 70 may be any type of material considered to be a disinfectant (or disinfectants), an aseptic (or aseptics), or a combination of one or more disinfectants with one or more aseptics. For purposed of the present invention, a "disinfectant" may be considered to be any substance or material that is generally effective for inactivating bacteria, viruses, or other non-sterile organisms. For purposed of the present invention, an "aseptic" may be considered to be any substance or material that lacks bacteria, viruses, or other non-sterile organisms (or bacteria, viruses, and other non-sterile organisms that are active or capable of being activated) but does not necessarily function to destroy bacteria, viruses, or other non-sterile organisms.

Apparatus 27 refers to an apparatus for applying a dressing that surrounds a target area 14 on a patient's body 13 in which the dressing provides a protective barrier from non-sterile contaminants. In the preferred embodiments of the present invention, one or more inner bags 10 are generally disposed or "nested" inside one or more outer bags 8. In the most preferred embodiments, one inner bag 10 is nested inside an outer bag 10. However, those skilled in the art will appreciate that the present invention also contemplates other embodiments such as multiple inner bags 10 that are nested inside an outer bag 8 or a scenario where more than one inner bag 10, with each inner bag being at least partially surrounded by an outer bag 8, have been applied to the same patient, in one or more areas to cover or enclose one or more target areas.

In the most preferred embodiments of the present invention, inner bag 10 of apparatus 27 comprises a sterile interior space 38 and a sterile exterior 12. In the most preferred embodiments, inner bag 10 and outer bag 8 are mainly constructed from transparent material 67, such as plastic. The use of an inner bag 10 and an outer bag 8 constructed of transparent material 67 allows the healthcare provider and the patient to see the target area 14 of patient's body 13, which is useful while inner bag 10 and outer bag 8 are being applied to patient's body 13. Additionally, the transparent nature of the material allows for monitoring of the target area while the patient is being transported from the pre-operative environment to the location where the selected procedure will be performed.

In other preferred embodiments of the present invention, inner bag 10 and outer bag 8 could be constructed from translucent material, substantially transparent material, and substantially translucent material. Alternatively, in certain embodiments of the present invention, where visibility of the target area is not required, opaque material may be used in the construction of inner bag 10 and outer bag 10. In the most preferred embodiments of the present invention, inner bag 10 is nested inside outer bag 8 at the time of manufacture and inner bag 10 and outer bag 8 come pre-packaged in a sterile package as a single device.

While not preferred, other embodiments of the present invention contemplate an inner bag 10 and an outer bag 8 that come in separate, sterile packages that are combined at the point of application to the target area. Yet even other embodiments of the invention contemplate an inner bag 10 and an outer bag 8 that is are sterilized at the facility where they will be deployed by the healthcare professional prior to application to a patient in the target environment. In this embodiment, the health care professional would then nest inner bag 10 inside outer bag 8.

In the most preferred embodiments, interior space 38 of inner bag 10 is sterile because interior space 38 of inner bag 10 will cover and/or surround a target area 14 of a patient's body 13; in the most preferred embodiments, the exterior 12 of inner bag 10 will also be sterile because outer bag 8 will be removed in the surgical room (or just prior to entering the surgical room) and exterior 12 of inner bag 10 will then be exposed. (The interior space 38 of inner bag 10 consists of the annular space 37 of inner bag 10 and the interior surface 11 of inner bag 10; likewise, the interior space 60 of outer bag 8 consists of the annular space of outer bag 8 and inner surface of outer bag 8.) Additionally, in the most preferred embodiments, interior surface 61 of outer bag 8 has been sterilized because interior surface 61 of outer bag 8 contacts (or comes near to contacting) exterior 12 of inner bag 10.

In the most preferred embodiments of the present invention, the user can attach cuff 30 of inner bag to a target area 14, that is, a surface area on the patient's body that needs to be sterilized or disinfected. Generally, target area 14 will be accessed by the surgeon just prior to performing the scheduled procedure, thus it is often advantageous to disinfectant target area 14 in a pre-surgical room. The apparatus comprises inner bag, outer bag, and multiple fasteners. In the most preferred embodiments these fasteners are selectively removable, selectively positionable, and selectively repositionable. In the most preferred embodiments there will be at least one adhesive mechanism, such as a body-fastener 58 and a bag-fastener 40.

Body-fastener 40 generally refers to an adhesive zone or adhesive mechanism that allows the user to temporarily attach cuff 30 of inner bag 10 to a contact-portion of the patient's body. In the most preferred embodiments, if the user of the apparatus wanted to slide inner bag 10 and outer bag 8 over the patient's foot, the medical worker could then temporarily affix cuff 30 of inner bag 10 to the knee of the patient, which could be termed the contact-portion of the patient's body. In this embodiment, the patient could be scheduled to undergo foot surgery and the contact-portion, which is the knee, of the patient's body does not need to be disinfected since the surgeon would not have to open up the knee. However, the contact-portion of the patient's body is generally an area on the patient's body in which the medical professional can fasten the body-fastener of inner bag (or outer bag in some embodiments) to the patient's body. Generally, the target area, that is the area of the patient's body that needs to be disinfected prior to surgery, will be adjacent to the contact-portion of the patient's body.

In certain preferred embodiments of the present invention, the body-fastener is a strap with a selectively repositionable hook and loop fastener (e.g. a strap with a Velcro® fastener) and is similar to the type of strap that is places around the patient's arm during a blood pressure examination. When measuring the patient's blood pressure, it is a common practice to temporarily affix the blood-pressure device to the patient's upper arm.

In yet another preferred embodiments of the present invention, the body-fastener is a simple strip of adhesive that lines cuff 30 and is covered with a plastic covering. The user can then remove the plastic covering and temporarily affix the cuff 30 to the contact-portion of the patient's body, much like healthcare professionals affix a Band-Aid to the skin of patients. In certain preferred embodiments of the present invention, Velcro® straps, adhesive strips, adhesive straps, zip-lock opening-closing devices, glue strips, combinations of the aforementioned adhesive mechanisms, or other mechanisms are used as fasteners to non-permanently attach the cuff 30 to the contact-portion of the patient's body.

In the most preferred embodiments of the present invention, outer bag 8 can be quickly and selectively detached from inner bag 10. In certain embodiments of the present invention, Velcro® straps, adhesive strips, adhesive straps, zip-lock opening-closing devices, glue strips, or other mechanisms are used as fasteners to temporarily attach outer bag 8 to inner bag 10, which would allow the health care professional using the device to quickly and easily detach outer bag 8 from inner bag 10 so that outer bag 8 could be discarded and inner bag 10 could remain temporarily attached to the patient (for purposes of explanation, these various fasteners may be termed "bag-fasteners"). One or more clasp-fasteners, such as a holding tab 72, could be constructed from virtually any material and could be fastened to the exterior 9 of outer bag 8. In the most preferred embodiments, a holding tab or holding tabs can be manually clasped by the healthcare professional's hand (or by a healthcare professional who is using an instrument such as tweezers). When the healthcare worker desires to remove outer bag 8, the healthcare worker can then grasp holding tab 72 to pull off outer bag 8 from inner bag 10 or grasp holding tab 72 while removing inner bag 10 from outer bag 8 so that inner bag 10 is no longer disposed, that is nested, within outer bag 8.

Figure 2:
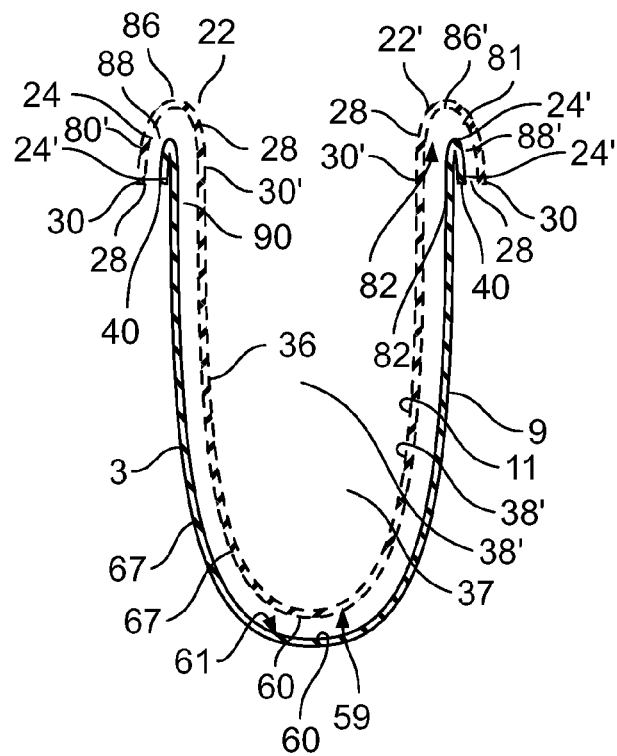
FIG. 2 is a cross-sectional view of inner bag and outer bag of the apparatus of FIG. 1 and FIG. 3.

Referring now to FIG. 1 and FIG. 2, a hem portion 28 of inner bag 10 is the portion of inner bag 10 that extends beyond cuff portion 24, 24' of outer bag 8. In the most preferred embodiments, cuff portion 30 comprises a hem 28 and outer bag 8, inner bag 10, cuff 30, and one or more fasteners are combined into a single barrier-dressing device 3. During assembly of the barrier-dressing device 3, hem 28 is folded back over, that is, doubled back over, defining both a fold-line 86 and cuff-portion 24, 24" of outer bag 8. Cuff 30 is approximately twice as long as the hem 28.

Cuff 30 most preferably comprises hem 28 as well as a portion of inner bag 10 that is approximately equal in length and area to hem 28, adjacent to hem 28 and fold-line 86, and that does not extend beyond outer bag 8. Cuff 30 is U-shaped so that cuff-portion 24, 24" of outer bag 8 can then be inserted down the middle of the cuff 30.

Once cuff-portion 24, 24" of outer bag 8 has been inserted down the middle of cuff 30 then, in the most preferred embodiments, if the cuff 30 is oriented in the same direction as the letter "U", then the combination of cuff 30 and cuff-portion 24, 24' of outer bag 8 resembles the letter "E" that has been rotated 90° in the counterclockwise direction (the main difference is that cuff-portion 24, 24' of outer bag 8 is usually not selectively attached to cuff 30, and if cuff-portion 24, 24' of outer bag 8 is selectively attached to cuff 30, then the cuff-portion 24, 24' is detachably attached to outer bag 8 so that outer bag 8 can be removed.)

Referring now to FIG. 2, a bag-fastener 40, 40' of cuff 30 is selectively configured to non-permanently attach outer bag 8 to inner bag 10. In the most preferred embodiments, bag-fastener 40, 40' non-permanently attaches an attaching-portion 88, 88 of exterior 9 of outer bag 8 to the distal interior 80, 80' of the cuff, which is coextensive with a portion of exterior 12 of inner bag 10, and/or non-permanently attaches a second attaching-portion 90, 90 of the interior space 60 of outer bag 8 to the proximate interior 82, 82 of cuff 30. Some non-limiting examples of fasteners that can be used in the most preferred embodiments include hook and loop (e.g., Velcro®) fasteners, zip-lock devices, strips of non-permanent glue, zippers, tie-strings, hooks and loops, and buttons and buttons holes.

In the most preferred embodiments of the present invention, there is at least one bag-fastener 40, 40' that temporarily attaches a portion of inner bag 10 to a portion of outer bag 8. In some embodiments, there may be a plurality of fasteners 40, 40' located on cuff 30 or on cuff-portion 24, 24' of outer bag 8. In certain other embodiments of the present invention, as long as the bag-fastener 40, 40' non-permanently attaches outer bag 8 to inner bag 10, then bag-fastener 40, 40' could be located on outer bag 8, on inner bag 10, or on both outer bag 8 and inner bag 10 in a distal location relative to cuff 30. In other embodiments, no bag-fastener 40, 40' is necessary and cuff-portion 24, 24' of outer bag 8 is inserted into cuff 30 and kept in place by gravity or by the folding of hem 28. In the most preferred embodiments, contact-portion 58 of patient's body 13 is not coextensive, that is, does not overlap, with target area 14 of patient's body 13 that is to be disinfected or sterilized and maintained in an aseptic condition.

Referring now to FIG. 1, the most preferred embodiments of the present invention contemplate the use of at least one aerating mechanism 2, that is, any mechanism that can be selectively configured to allow one or more disinfectants or antiseptics to pass through the aerating mechanism 2 and that causes the one or more disinfectants or the one or more antiseptics to mix with air and form foam 4 or a foamy-like substance. The foam 4 or foamy-like substance still retains its disinfecting or antiseptic properties. In at least one preferred embodiment of the present invention, sterile substance 70 comprises a liquid or vapor that is directly applied to the interior space 38 of inner bag 10; however, one advantage of using aerating mechanism 2 is that foam 4 will generally weigh less than liquid, which configures device 88 filled with foam 4 in such a way that a healthcare worker can more easily handle device 88 filled with foam 4 then if device 88 was filled with liquid.

Some non-limiting examples of aerating mechanism 2 are air stones such as those that are typically used in fish aquariums and are comprised of materials such as lime wood, porous stones, bonded glass beads, and/or fiberglass. Air stones of various shapes, sizes, and levels of coarseness could be used, depending on the application and variables such as the air-liquid ratio, viscosity of the disinfectant, size of tubing used to deliver the combined air/disinfectant stream, etc. In the most preferred embodiments, aerating mechanism 2 is detachably coupled to the tip of a coupling mechanism because aerating mechanism 2 and coupling mechanism 92 can be jointly inserted into interior space 38 of inner bag 10.

In the most preferred embodiments of the present invention, coupling mechanism 92 comprises one or more lengths of hose or tubing 50 which are selectively configured to couple an air delivery mechanism (e.g., air pump) 52 with interior space 38 of inner bag 10 or interior 60 of outer bag 8. The tubing may be selectively configured to transport one or more substances; these substances generally comprise sterile substances 70 and, in certain embodiments, non-sterile substances. The tubing of the apparatus is configured to allow substances to move through the tubing, much like a rubber hose is configured to allow fluid to travel through the hose. In the most preferred embodiments of the present invention, tubing 50 is transparent and flexible and the tubing is configured so that it can allow substances, under controlled pressure, to travel through the tubing.

The following list of substances and pressures comprises substances and types of pressures that the pump can pump, that is cause to move through, tubing, is non-limiting and non-exhaustive: disinfectants, antiseptics, air, gases, vapors, mists, liquids, fluids, moistures, foams, gels, nanoparticles, particles, molecules, pressure, negative pressure, positive pressure, ambient pressure, equilibrium pressure, dynamic pressure, vapor pressure, stagnation pressure, surface pressure, and combinations of the aforementioned objects and types of pressure. In at least one preferred embodiment of the present invention, one or more lengths of tubing 50 are connected to one or more optional valves 15.

In certain preferred embodiments of the present invention, a single length of tubing 50 may be used to connect the pump with inner bag and outer bag; however, in other embodiments, a length of tubing could be connected to a valve and the valve could be connected to another length of tubing. Alternatively, the length of tubing may branch off, and form a "T-connection"; one part of the tubing could be connected to the plastic bag or container, which has an interior space, filled with disinfectant of an IV system and the other part of the tubing could travel through a flow port and into an inner bag.

In at least one preferred embodiment of the present invention, valves 15 are embedded within the one or more lengths of tubing 50. In other preferred embodiments of the present invention, a valve 15 is configured to regulate the flow of sterile substance 70 through the tubing 50; a non-limiting example is a one-way valve 15 that prevents the backflow of the sterile substance 70 up the tubing 50 and towards the pump 52. In some non-limiting embodiments, valves 15 are adjustable so that the user can control the rate of flow for sterile substance 70 into interior space 38 of inner bag 10 (and/or into interior 60 of outer bag 8).

In the most preferred embodiments of the present invention, tubing 50 may also be configured to deliver disinfectants, antiseptics, air, gases, vapors, mists, liquids, fluids, moistures, foams, gels, nanoparticles, particles, molecules, pressure, negative pressure, positive pressure, ambient pressure, equilibrium pressure, dynamic pressure, vapor pressure, stagnation pressure, surface pressure, and combinations of the aforementioned objects and types of pressure. In the most preferred embodiments the pump introduces substances and types of pressure into inner bag via the tubing, in other words, the pump causes substances and types of pressure to travel through tubing and travel into the interior space of inner bag.

Alternatively, pump can create a vacuum and suck substances and types of pressure from inner bag. In this application, the pump can create a negative pressure gradient that will induce fluids, substances, and other pressures, to exit inner bag, travel through the tubing, and then enter some type of waste container, bag, or bowl. In some preferred embodiments of the present invention, a first pump is used to pump fluid through the tubing and into inner bag and a second pump is used to create a negative pressure gradient that will induce excess foam to leave inner bag and travel through tubing 50. In the most preferred embodiments the pump is a versatile pump and is configured to alternately pump materials into inner bag 10 and also to extract materials from within inner bag 10.

One or more pumps 52 are generally used in the preferred embodiments; the one or more pumps 52 can be selectively configured to pump air, gas, vapor, mist, liquid, fluid, moisture, foam 4, gels, particles, negative pressure, positive pressure, ambient pressure, equilibrium pressure, dynamic pressure, vapor pressure, stagnation pressure, and surface pressure, other types of matter, and combinations thereof into interior space 38 of inner bag 10 and/or interior 60 of outer bag 8.

In the most preferred embodiments apparatus 88 has one or more flow ports 42. The one or more flow ports 42 are selectively configured to allow the length(s) of tubing 50 to pass through the one or more flow ports 42 and into interior space 38 of inner bag 10 and/or the interior space 60 of outer bag 8. In the most preferred embodiments, the one or more flow ports 42 are configured to allow one or more length(s) of tubing 50 and aerating mechanism 2, which is connected to the tip of tubing 50, to pass through an annular space that is located between cuff 30 and patient's body 13. In some preferred embodiments of the present invention, the one or more flow ports 42 are selectively configured to allow one or more lengths of tubing to pass through outer bag and/or inner bag and into the interior of inner bag at a point that is distal from the cuff. In the preferred embodiment of the invention, apparatus 27 comprises an IV system, in which the disinfectant and/or aseptic is contained in a container such as a bottle or bag and then the force of gravity causes the disinfectant and/or aseptic to drip down the tubing and into the first end of a T-shaped area of the tubing where a second end of the T-shaped area of the tubing is connected with the pump and the third end of the T-shaped area is connected with tubing, and the tubing travels through the flow port and into the interior of inner bag.

In this embodiment, the disinfectant and/or aseptic is then pumped into the interior of inner bag. In another embodiment one or more zip-lock open-closing devices are located on inner bag and/or outer bag. The zip-lock open-closing device(s) can be used to close the cuff so that it stays snug against the patient's body 13 but not permanently attached to the contact-portion 58 of the patient's body 13. In the most preferred embodiments the pump is first used to introduce a substance such as a disinfectant into the interior space of inner bag. In some embodiments, the pump sends a packet of air (or fluid) through the tubing and the force of the moving air (or fluid) can be used to carry (or move) other objects through the tubing and into the interior space of inner bag.

Generally, the tubing is inserted into the interior of inner bag and has an aerating mechanism, such as an air stone, that is attached to the tip of the tubing. In the most preferred embodiments, the pump causes a fluid that is a disinfectant to travel through the tubing. The fluid exits the tip of the tubing and then enters the aerating mechanism, such as an air stone. In the most preferred embodiments, as the fluid travels through the tubing, the fluid is being mixed with air, and as the mixture of fluid and air moves through the pores of the air stone, a foam or an aerated bubble-like substance is formed. In certain preferred embodiments of the present invention, the mixing of fluid and air primarily occurs within the pores of the air stone or other aerating mechanism. In the most preferred embodiments, the amount of foam can be increased so that inner bag 10 and outer bag 8 inflate and resemble to an inflated balloon. In certain embodiments of the present invention, substances may be pumped into the interior space of outer bag, and foam may also be used to fill the interior space of the outer bag.

In the most preferred embodiments of the invention, the pump can then be used to apply negative pressure and extract any excess foam from inner bag 10. Generally, after the excess foam has been removed, the pump can then be used to apply negative pressure, thereby creating a mild vacuum within inner bag 10 and thereby inducing the interior of inner bag 10 to adhere to the target area. Generally, in the most preferred embodiments of the present invention, after the patient has been transported into the surgery room the pump may be used to apply positive pressure to the interior space of inner bag 10 so outer bag 8 and inner bag 10 can be removed just prior to surgery.

In at least one preferred embodiment of the present invention, the target area of the patient's body is a relatively flat surface, such as a chest or a thigh. In these applications, a multiple layer sterile dressing may be substituted for the nested bags described above. For these situations, the target area is not inserted into a bag but is instead covered with the multiple layer sterile dressing with the aeration mechanism being places in close proximity to the target area, under the multiple layer sterile dressing. The edges of the multiple layer sterile dressing may be temporarily affixed to the target area of the patients body by adhesive material and the like, with the layers of the multiple layer sterile dressing serving the same purposes and being used in substantial conformance to the nested bags previously described.

However, in other preferred embodiments of the present invention, the inner and outer bags are designed so that one or more target areas of the patient's body can be inserted through the opening of the bag into the interior space of the inner bag. Some non-limiting examples of target areas of a patient's body that could be inserted through an opening of inner bag 10 include: one or more body parts, limbs, one or more arms, one or more elbows, one or more fingers, one or more toes, one or more ears, one or more genitals, one or more buttocks, a nose, a chin, a forehead, one or more one wrists, one or more palms, one or more hands 5, one or more legs, one or more knees, a chest, a torso, an abdomen, one or more shoulders, a back, a head, a face, a neck, and at least one foot.

Figure 3:
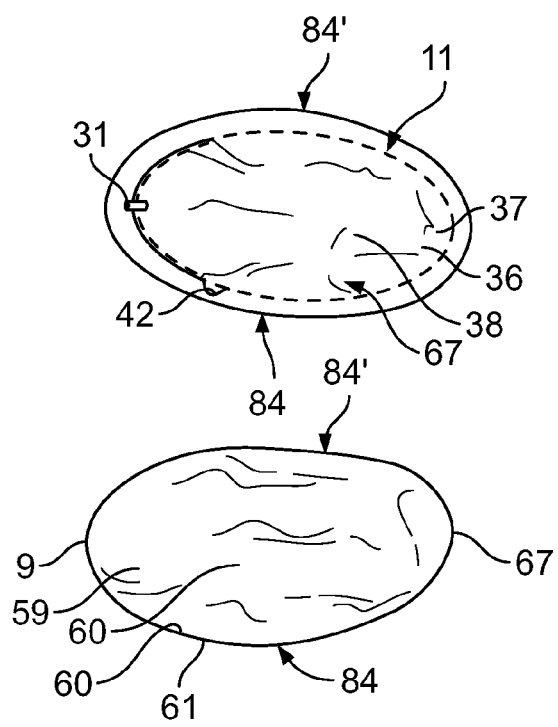
FIG. 3 is a bottom view of inner bag and outer bag of the apparatus after outer bag has been removed from inner bag.

Referring now to FIG. 3, a bottom view of inner bag 10 and a bottom view of outer bag 8 are shown. Outer bag 8 has either been removed from inner bag 10 (after outer bag has already been inserted onto inner bag); alternatively, FIG. 3 depicts a most preferred embodiment before the cuff has been assembled at the factory, that is, before inner bag has been inserted into the interior space 60 of outer bag Band/or outer bag has been inserted onto the exterior of inner bag 10 so that it partially-surrounds inner bag. The reason that in the most preferred embodiments inner bag 10 is only partially-surrounded by outer bag, and not completely surrounded by outer bag 8, is that the opening of inner bag 10 should be exposed; otherwise, a patient's target area could not be enclosed by inner bag 8.

Different sizes and shapes of embodiments of the bags described herein may be used in conjunction with the various preferred embodiments of the present invention. The following dimensions are provided as non-limiting examples of the size of inner bag orifice as well as the intended application. In one preferred embodiment of the present invention, inner bag orifice has a circumference of 10 cm, a length of 12 cm, and is intended for use with a pediatric foot lower leg or a hand-lower arm. In another preferred embodiment of the present invention, inner bag orifice has a circumference of 10 cm, a length of 17 cm, and is intended for use with a pediatric foot-upper leg or a hand-upper arm. In yet another preferred embodiment of the present invention, inner bag orifice has a circumference of 16 cm, a length of 21 cm, and is intended for use with a small foot-lower leg or a hand-lower arm.

In still another preferred embodiment of the present invention, inner bag orifice has a circumference of 10 cm, a length of 24 cm, and is intended for use with an extra-small foot-upper leg or a hand-upper arm. In yet another preferred embodiment of the present invention, inner bag orifice has a circumference of 16 cm, a length of 24 cm, and is intended for use with a medium lower leg or a hand-lower arm. In another embodiment inner bag orifice has a circumference of 16 cm, a length of 28 cm, and is intended for use with a medium foot-upper leg or hand-upper arm. In another embodiment inner bag's 10 orifice 22, 22 has a circumference of 16 cm, a length of 32 cm, and is intended for use with a medium long foot-upper leg or a hand-upper arm.

In yet another preferred embodiment of the present invention, inner bag orifice has a circumference of 20 cm, a length of 28 cm, and is intended for use with a large foot-lower leg or a hand-lower arm. In still another preferred embodiment of the present invention, inner bag orifice has a circumference of 20 cm, a length of 35 cm, and is intended for use with large foot-upper leg or hand-upper arm. In another embodiment inner bag orifice has a circumference of 20 cm, a length of 39 cm, and is intended for use with a large extra-long foot-upper leg or a hand-upper arm. In another embodiment inner bag orifice has a circumference of 28 cm, a length of 44 cm, and is intended for use with an extra-large foot-upper leg or a hand-upper arm.

Figure 4:
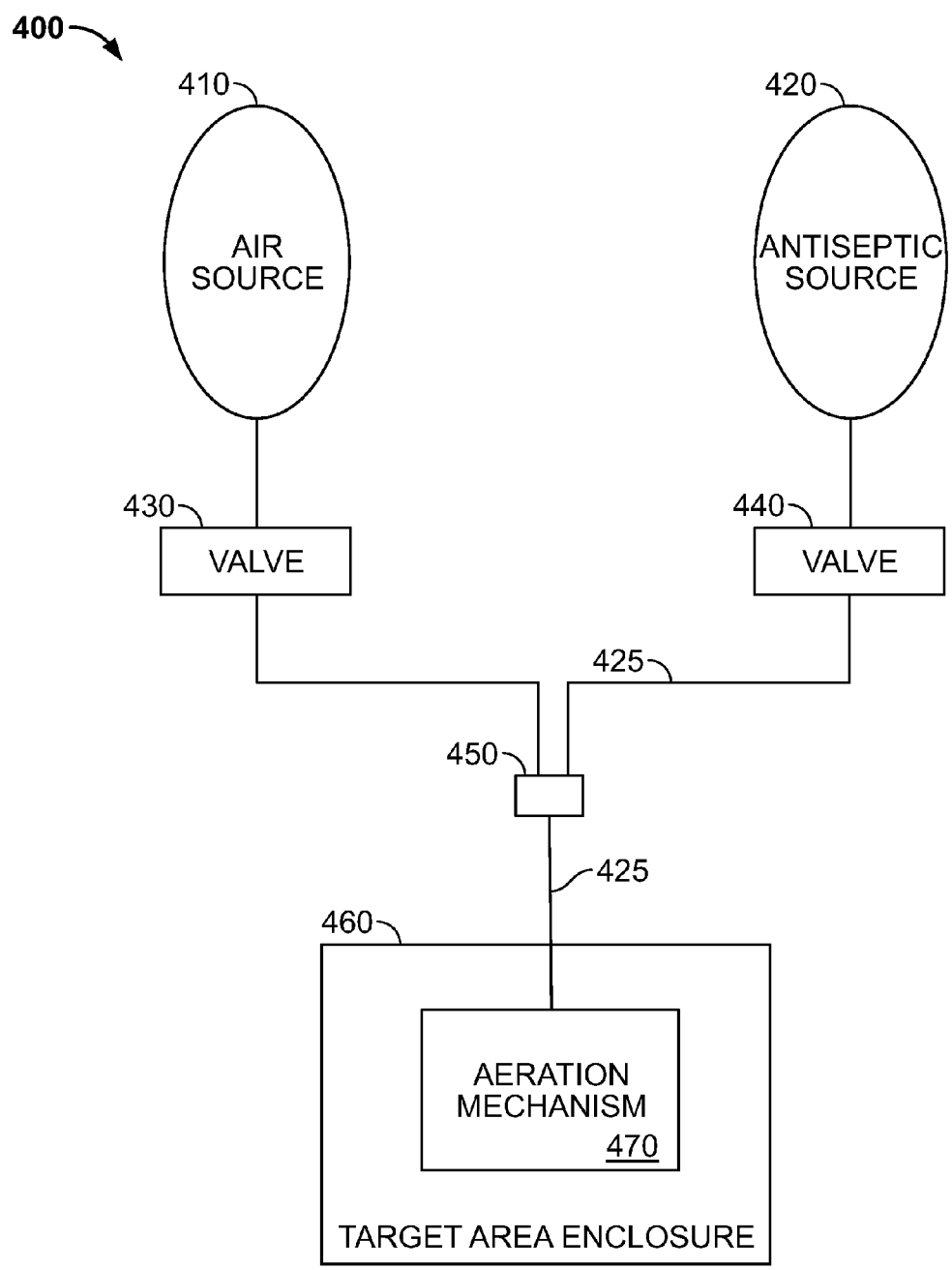
FIG. 4 is a schematic diagram of the various components of an apparatus used for a method of sterilization in accordance with a preferred embodiment of the present invention.

Referring now to FIG. 4, a sterilization apparatus 400 in accordance with a preferred embodiment of the present invention comprises: an air source 410; an antiseptic or disinfectant source 420; an optional valve 430; an optional valve 440; a connector 450; an aeration mechanism 470 and a target area enclosure 470, all being communicatively coupled via tubing 425.

Air source 410 may be any type of air pump or air transfer device capable of pumping air into tubing 425. This may comprise, for example and not by way of limitation, an aquarium style air pump or a compressed air delivery system such as those found in many hospital pre-operative rooms and surgical theaters. In general, most hospital and clinic preoperative staging areas, operating rooms and recovery rooms are provided with suction devices that are suitable for creating a vacuum that is compatible with the most preferred embodiments of the present invention. Additionally, compressed air is generally available in most surgery theaters and oxygen in available in all relevant areas.

Antiseptic source 420 is any storage and delivery mechanism for storing and delivering an appropriate antiseptic or disinfectant material to tubing 425. In at least one preferred embodiment of the present invention, antiseptic source 420 is a standard IV drip bag containing a commonly used pre-operative surgical antiseptic solution used for pre-operative sterilization of the target area.

Valves 430 and 440 may be any type of valve known to those skilled in the art, including without limitation, thumb controllable "wheel" valves, ball valves, drip valves, etc. The function of valves 430 and 440 is to control the rate of flow for the air and the antiseptic solution flowing into aeration mechanism 470 so as to provide the optimal mixture of air and antiseptic solution for delivery to the target area.

Connector 450 is most preferably a "T" style union or connector that joins the tubing 425 that is delivering air from air source 410 and the tubing 425 that is delivering antiseptic solution from antiseptic source 420 into a single piece of tubing 425. The combined flow air and antiseptic stream is introduced into aeration mechanism 470 via another section of tubing 425.

Target area enclosure 460 is configured to isolate the target area from neighboring areas and from contact with other possible sources of contamination. As previously explained, in at least one preferred embodiment of the present invention, target area enclosure 460 is a set of sterile bags, with a first bag being positioned with a second bag. By utilizing a double bag or double layer of protection, the target area can be sterilized in a pre-operative environment. After sterilization has been completed, the patient may be transported to the operating room for the necessary procedure.

Aeration mechanism 470 is contained within target area enclosure 460 and is configured to create a foaming substance from the mixture of air from air source 410 and the antiseptic solution. The resultant foamy substance will coat the target area, effectively sterilizing the target area so as to ensure a sterile environment for the planned medical procedure. Aeration mechanism 470 may be any type of device known to those skilled in the art that is capable of producing a foamy substance from the combined air and antiseptic delivered from air source 410 and antiseptic source 420. In at least one preferred embodiment of the present invention, aeration mechanism 470 is a standard aquarium air stone that is coupled to tubing 425 and contained within target area enclosure 460.

Figure 5:
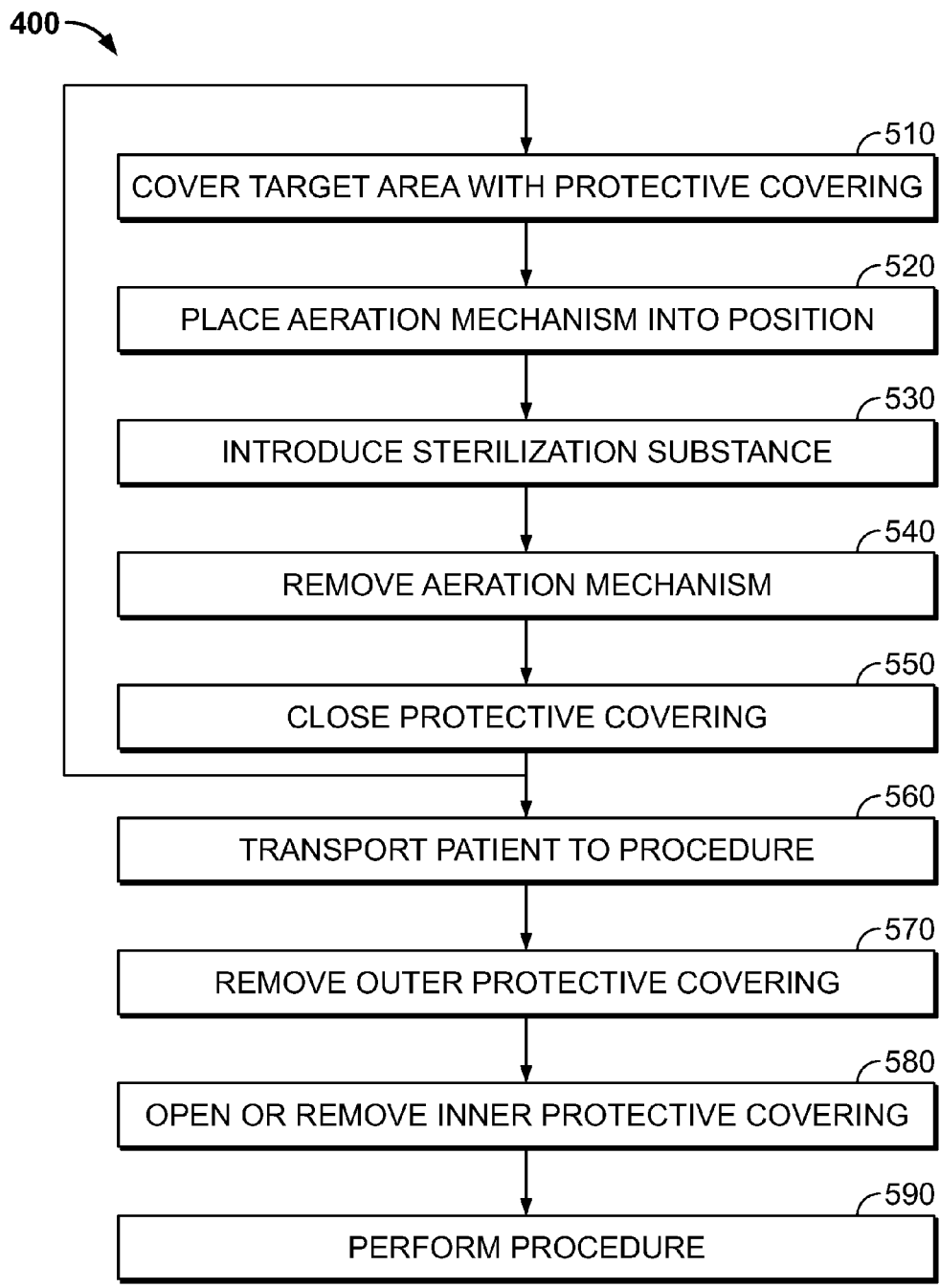
FIG. 5 is a flow chart of a method of using an apparatus for sterilization in accordance with a preferred embodiment of the present invention.

Referring now to FIG. 5, a flowchart for a method 500 for accomplishing sterilization of a target area in accordance with a preferred embodiment of the present invention is depicted. As shown in FIG. 5, the target area is covered with a single-layer or multi-layer protective covering (step 510). As described above, this may be a series of nested bags or a multiple layer dressing that is applied over and/or around the target area that is to be sterilized. Next, the aeration mechanism is positioned within the protective covering, in close proximity to the target area (step 520) and the sterilization substance is introduced into the area between the protective covering and the target area (step 530), thereby inducing the sterilization substance to contact the target area, effectively disinfecting and sterilizing the target area.

Once the proper amount of sterilization substance has been introduced, the aeration mechanism may be removed from within the protective covering (step 540) and the protective covering may be closed off to prevent any contaminants from entering into the protective covering and contacting the target area (step 550). As shown in FIG. 5, this process may be repeated for multiple target areas on a single patient, if desired or necessary, depending on the contemplated procedure or procedures.

With the protective covering securely in place, and with the aeration mechanism removed, the patient is ready to be transported to the room or suite where the procedure will be performed (step 560). When it is time to begin the procedure, the outer layer of the protective covering may be removed (step 570). Step 570 may be performed just prior to entering the room or suite where the procedure is to be performed, if desired. With the outer layer of protective covering removed, the medical personnel may open or remove the inner layer of the protective covering (step 580) and perform the scheduled procedure (step 590).

Figure 6:
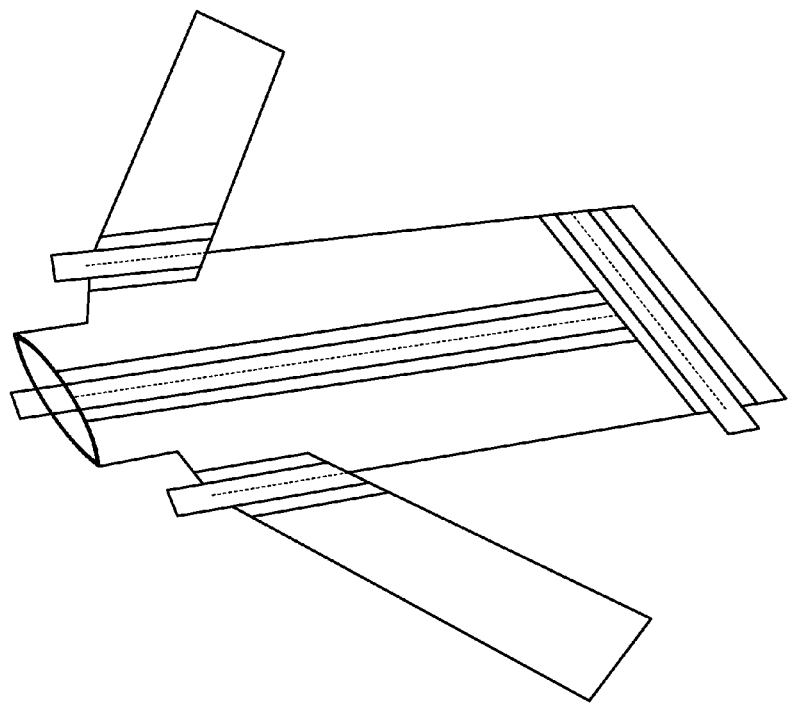
FIG. 6 is a schematic drawing of a disposable garment top for use in sterilization activities in accordance with an alternative preferred embodiment of the present invention.

Referring now to FIG. 6, a disposable garment top 600 for use in sterilization procedures in accordance with an alternative preferred embodiment of the present invention is depicted. In the most preferred embodiments of the present invention, garment top 600 is fabricated from a durable, yet lightweight disposable plastic material that can be manufactured in a process that produces clothing-like garments. In this case, garment top 600 may be manufactured in multiple standard sizes (e.g., small, medium, large, etc.) according to the various body types and sizes that may require sterilization of one or more target areas prior to undergoing surgical procedures.

In the most preferred embodiments of the present invention, garment top 600 will be manufactured with perforated seams that form "tear-off" or "tear-open" components, allowing for quick and easy access to the previously identified target areas after sterilization has been completed. As shown in FIG. 6, garment top 600 has a plurality of perforated reinforced seams 610 that are strategically placed along the arm openings, at the waist, and along the front of the garment. It is also anticipated that the back of garment top 600 may also be configured with a perforated and reinforced seam along the back as well (not shown this FIG.), parallel to and opposite the perforated reinforced seam on the front of garment top 600. Seams 610 are provided so that garment top 600 can be opened up and or removed without the necessity of completely removing garment top 600 from the body of the patient once the sterilization of the target area has been accomplished.

In addition, each of the perforated seams 610 of garment top 600 will be most preferably covered with a "release" tape 620 that serves at least two important purposes. First, release tape 620 provides a protective barrier or seal that minimizes or prevents any external environmental contaminants from entering into garment top 600 via perforated seams 610. Second, release tape 620 provides an additional structural element that prevents the separation of the various components of garment top 600 prior to the desired time. Further, an attachment portion 630 may be provided so as to allow garment top 600 to be securely taped or otherwise fastened to the patient's body, thereby securing garment top 600 in place.

In practice, garment top 600 will be placed over a patient who is scheduled to undergo a surgical or other medical procedure that requires the sterilization of a target area that will be covered by garment top 600. As previously explained above, a sterilization. In at least one alternative preferred embodiment of the present invention, the sterilization solutions will be prepackaged inside garment top 600, thereby obviating the need for the introduction of a sterilization substance into garment top 600.

Once the patient has donned garment top 600 and the target areas have been appropriately sterilized by contact with a sterilization substance, the patient will continue to wear garment top 600 until it is time for the procedure to take place. This allows the patient to be prepared for the procedure well in advance, thereby ensuing a more timely and successful preparation process.

In this fashion, a patient may assist in the sterilization process prior to receiving anesthesia and it will be easier to accomplish the pre-operative sterilization of the target area(s) in a pre-operative environment. Additionally, the disinfected target areas will be protected from inadvertent contamination during the transport of the patient from the pre-operative environment into the surgical theater or operating room. Once the patient has entered the surgical environment, release tapes 620 on garment top 600 may be removed, exposing perforated seams 610. The operating room personnel may then open and or remove the desired portions of garment top 600, thereby exposing the desired target areas of the patient.

Figure 7:
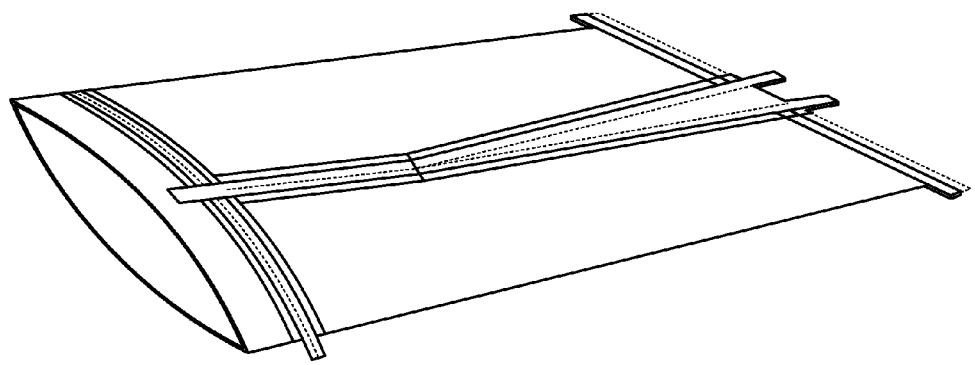
FIG. 7 is a schematic drawing of a disposable garment bottom for use in sterilization activities in accordance with an alternative preferred embodiment of the present invention.

Referring now to FIG. 7, a disposable garment bottom 700 for use in sterilization procedures in accordance with an alternative preferred embodiment of the present invention is depicted. In the most preferred embodiments of the present invention, garment bottom 700 is fabricated from a durable, yet lightweight disposable plastic material that can be manufactured in a process that produces clothing-like garments. In this case, garment bottom 700 may be manufactured in multiple standard sizes (e.g., small, medium, large, etc.), according to the various body types and sizes that may require sterilization of one or more target areas prior to undergoing surgical procedures.

In the most preferred embodiments of the present invention, garment bottom 700 will be manufactured with perforated seams that form "tear-off" or "tear-open" components, allowing for quick and easy access to the previously identified target areas after sterilization has been completed. As shown in FIG. 7, garment bottom 700 has a plurality of perforated reinforced seams 710 that are strategically placed along the arm openings, at the waist, and along the front of the garment. It is also anticipated that the back of garment bottom 700 may also be configured with a perforated and reinforced seam along the back as well (not shown this FIG.), parallel to and opposite the perforated reinforced seam on the front of garment bottom 700. Seams 710 are provided so that garment bottom 700 can be opened up and or removed without the necessity of completely removing garment bottom 700 from the body of the patient once the sterilization of the target area has been accomplished.

In addition, each of the perforated seams 710 of garment bottom 700 will be most preferably covered with a "release" tape 720 that serves at least two important purposes. First, release tape 720 provides a protective barrier or seal that minimizes or prevents any external environmental contaminants from entering into garment bottom 700 via perforated seams 710. Second, release tape 720 provides an additional structural element that prevents the separation of the various components of garment bottom 700 prior to the desired time. Further, an attachment portion 730 may be provided so as to allow garment bottom 700 to be securely taped or otherwise fastened to the patient's body, thereby securing garment bottom 700 in place.

In practice, garment bottom 700 will be placed over a patient who is scheduled to undergo a surgical or other medical procedure that requires the sterilization of a target area that will be covered by garment bottom 700. As previously explained above, a sterilization. In at least one alternative preferred embodiment of the present invention, the sterilization solutions will be prepackaged inside garment bottom 700, thereby obviating the need for the introduction of a sterilization substance into garment bottom 700.

Once the patient has donned garment bottom 700 and the target areas have been appropriately sterilized by contact with a sterilization substance, the patient will continue to wear garment bottom 700 until it is time for the procedure to take place. This allows the patient to be prepared for the procedure well in advance, thereby ensuing a more timely and successful preparation process.

In this fashion, a patient may assist in the sterilization process prior to receiving anesthesia and it will be easier to accomplish the pre-operative sterilization of the target area(s) in a pre-operative environment. Additionally, the disinfected target areas will be protected from inadvertent contamination during the transport of the patient from the pre-operative environment into the surgical theater or operating room. Once the patient has entered the surgical environment, release tapes 720 on garment bottom 700 may be removed, exposing perforated seams 710. The operating room personnel may then open and or remove the desired portions of garment bottom 700, thereby exposing the desired target areas of the patient.

Figure 8:
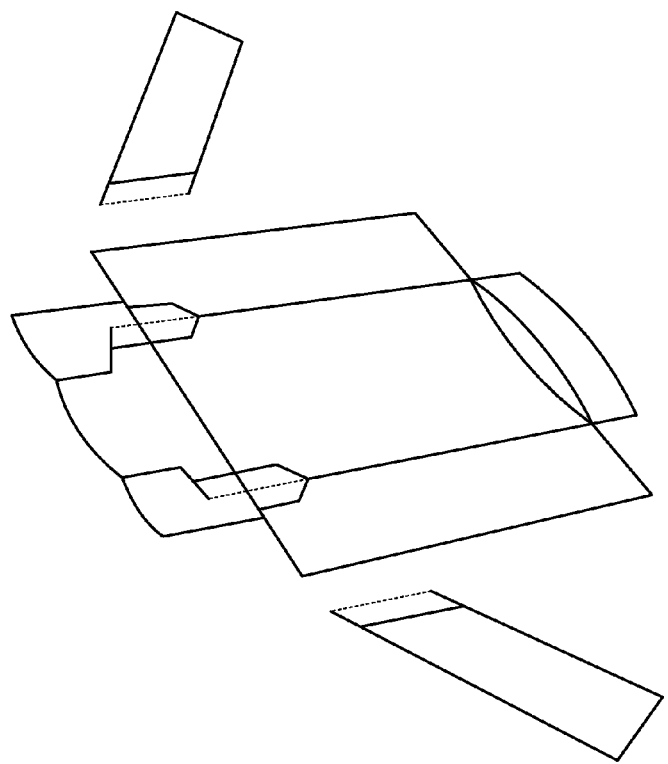
FIG. 8 is a schematic drawing of a disposable garment top for use in sterilization activities in accordance with an alternative preferred embodiment of the present invention.

Referring now to FIG. 8, garment top 600 of FIG. 6 is depicted after it has been opened, along seams 610. After having been opened along seams 610, the arm portions may be removed, if desired. In this fashion, the desired target areas can be exposed for the necessary procedure to take place.

Figure 9:
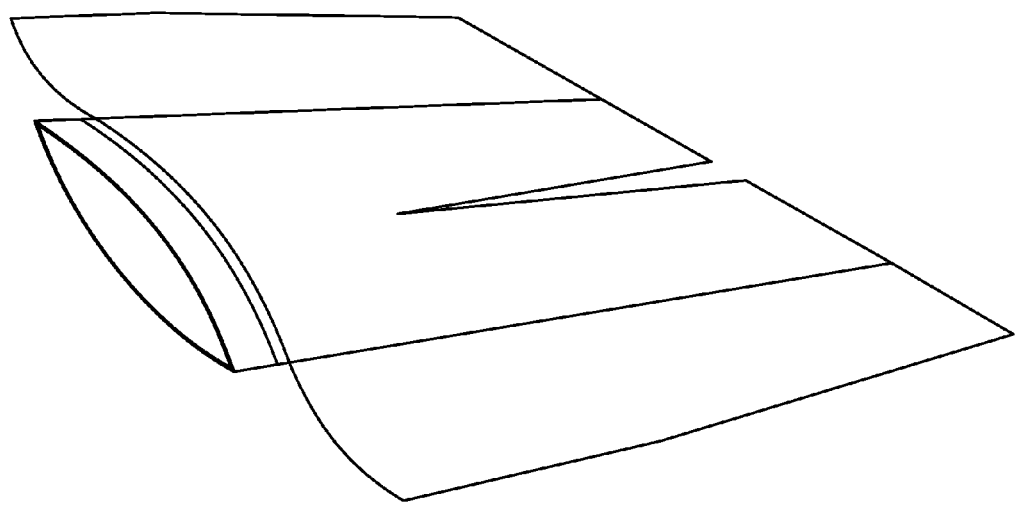
FIG. 9 is a schematic drawing of a disposable garment bottom for use in sterilization activities in accordance with an alternative preferred embodiment of the present invention.

Referring now to FIG. 9, garment top 700 of FIG. 7 is depicted after it has been opened, along seams 710. After having been opened along seams 710, the desired target areas can be exposed for the necessary procedure to take place.

Figure 10:
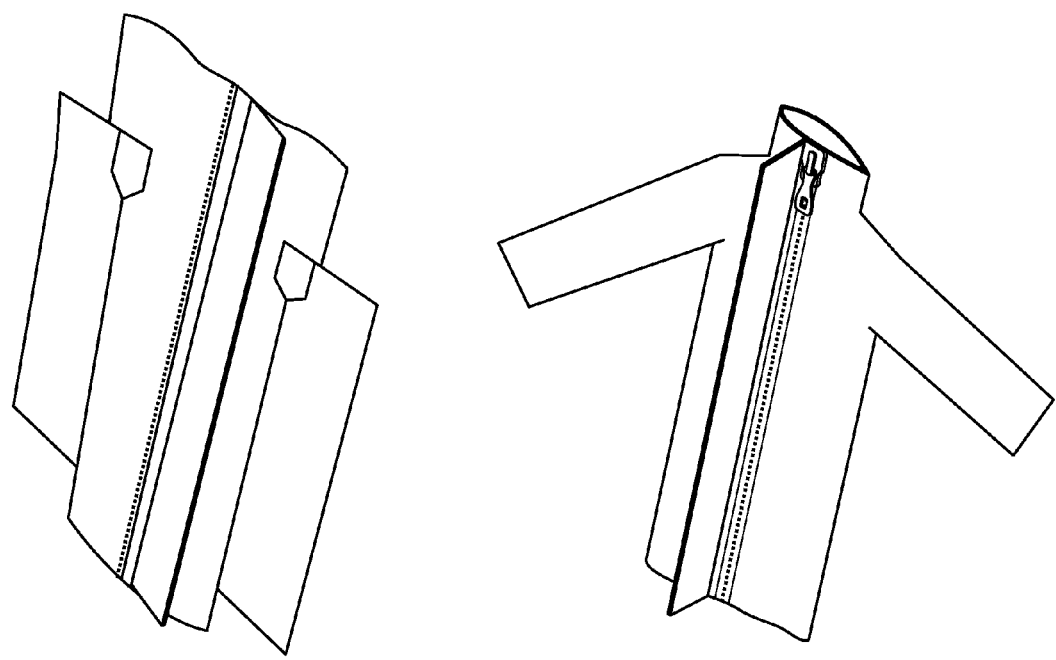
FIG. 10 is a schematic drawing of a disposable garment top with closure mechanisms for use in sterilization activities in accordance with an alternative preferred embodiment of the present invention.

Referring now to FIG. 10, a garment top 1000 in accordance with an alternative preferred embodiment of the present invention is depicted. In this preferred embodiment of the present invention, perforated seams 610 of FIG. 6 have been replaced by a "zip-lock" mechanism 1010 and release tapes 620 have been replaced by a repositionable and re-fastenable strip 1020 that can be folded over zip-lock mechanism 1010 as desired.

Figure 11:
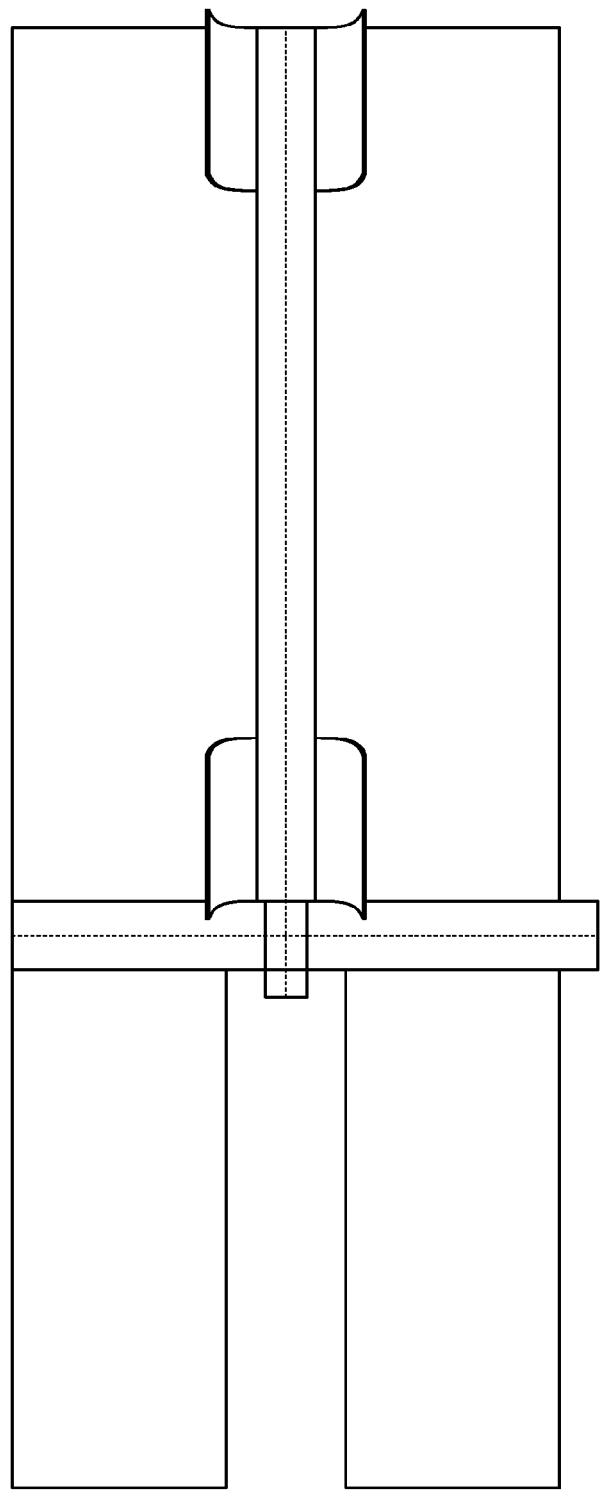
FIG. 11 is a schematic drawing of a disposable garment bottom with tab mechanisms for use in sterilization in accordance with an alternative preferred embodiment of the present invention.

Referring now to FIG. 11, garment bottom 700 of FIG. 7 has been provided with optional "pull tabs" 1130. Pull tabs 1130 are used to position garment bottom 700 over the patient and will allow medical personnel to handle and remove all or portions of garment bottom 700 as may be desired or necessary without contaminating the disinfected target areas being protected by garment bottom 700.

Figure 12:
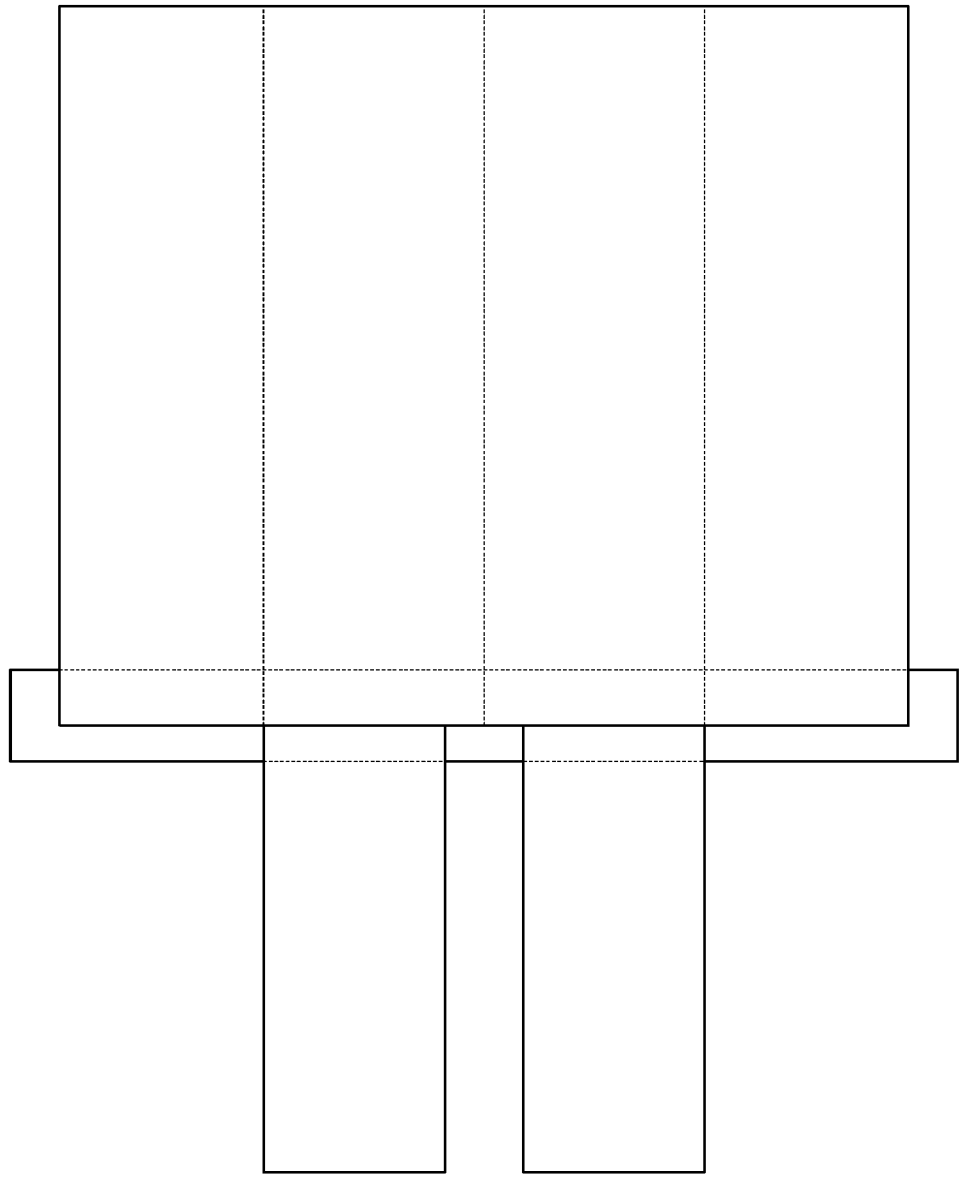
FIG. 12 is a schematic drawing of a disposable garment bottom with adhesive positioned for use in sterilization in accordance with an alternative preferred embodiment of the present invention.

Referring now to FIG. 12, attachment mechanism 1210 (e.g., adhesive tape) is shown as used to attach garment top 600 and/or garment top 700 to the patient's body. Attachment mechanism 1210 may be strategically positioned wherever it is needed to ensure that garment top 600 and/or garment top 700 remain securely in place until the patient is ready to undergo the necessary procedure.

Figure 13:
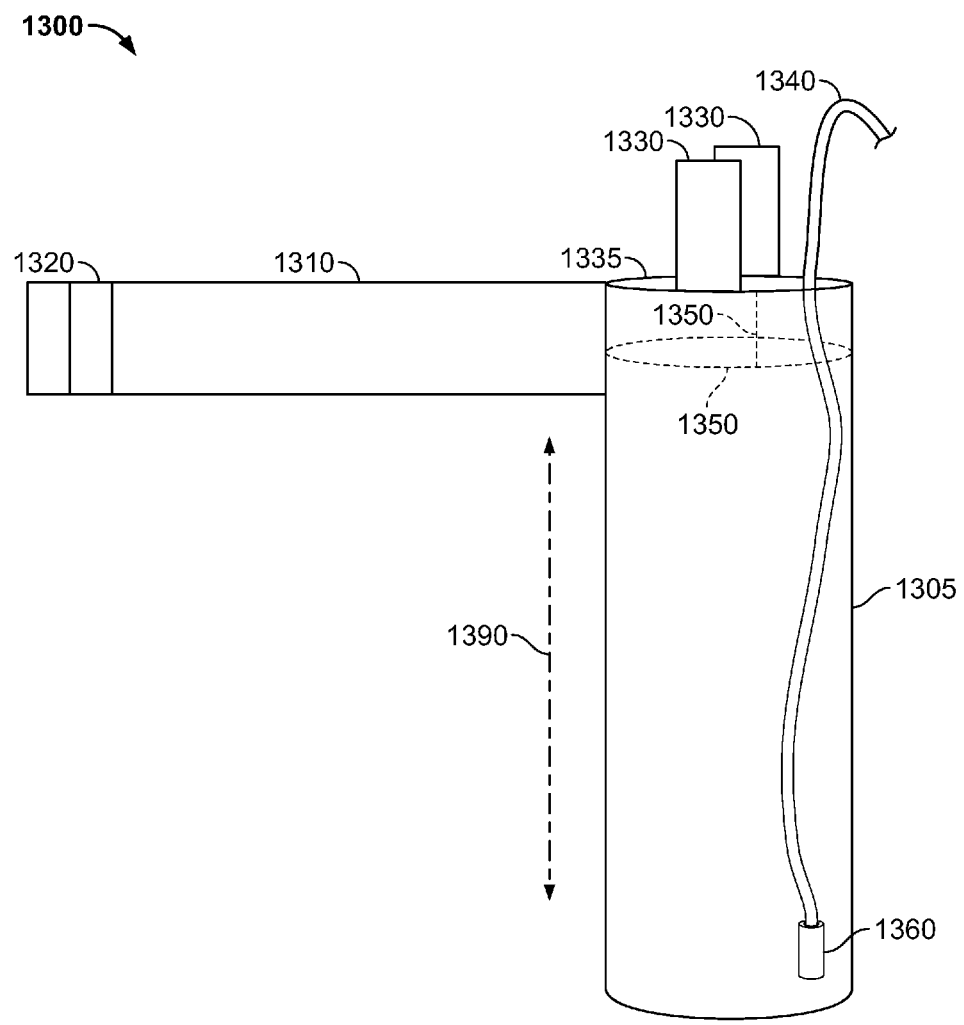
FIG. 13 is a schematic diagram of an apparatus for use in sterilization activities in accordance with an alternative preferred embodiment of the present invention.

Referring now to FIG. 13, an apparatus 1300 for use in sterilization activities in accordance with an alternative preferred embodiment of the present invention is depicted. As shown in FIG. 13, apparatus 1300 most preferably comprises a body 1305, an opening 1335 that is configured to provide access into the interior space of body 1305, a strap 1310 attached to body 1305, at least one but preferably two tabs 1330 attached to body 1305, an adhesive zone 1320 on strap 1310, and a pair of perforated seams 1350.

In addition, a delivery system for providing antiseptic or disinfectant into the interior space of body 1305 is depicted. As explained above in conjunction with FIG. 4, the most preferred embodiments of the delivery system typically comprises a tubing 1340 and an aeration mechanism 1360 affixed or attached to tubing 1340 and attached to one or more pumps as shown in FIG. 4 (not shown this FIG.).

As shown in FIG. 13, first perforated seam 1350 is substantially parallel with a longitudinal axis 1390 of body 1305. Second perforated seam 1350 is positioned around the circumference of body 1305 and substantially perpendicular the first perforated seam 1350. When deploying apparatus 1300, the patient will place their appendage (e.g., arm, leg, etc.) into opening 1335 of body 1305.

Once the appendage has been positioned within the interior space of body 1305, strap 1310 can be wrapped around the appendage and body 1305 and secured by affixing adhesive zone 1320 to body 1305. Once strap 1310 has been wrapped around the appendage and secured to body 1305, the antiseptic or disinfectant can be introduced into the interior space of body 1305 via the delivery system. As previously explained, this will serve to sterilize the appendage that has been secured inside body 1305. From this point forward, the patient can be transported to the location where the planned procedure can be performed.

The antiseptic may be introduced into the interior of body 1305 via the delivery system prior to securing the device first and then strap 1310 will be secured around the appendage and adhered to body 1305 by deploying adhesive zone 1320. This procedure will allow excessive air to be evacuated from the interior of body 1305, thereby enhancing the surface contact of the antiseptic with the skin of the patient. However, it is also possible that the antiseptic may be introduced into the interior of body 1305 after strap 1310 has been positioned and tightened in place.

Prior to performing the procedure, body 1305 can be removed from the patient by firmly grasping tabs 1330 and pulling the bottom portion of body 1305 in a direction that is substantially parallel to axis 1390, causing a tear along second perforated seam 1350, thereby exposing the appendage.

Tubing 1340 and an aeration mechanism 1360 comprise a delivery system for delivering antiseptic or disinfectant to the desired location within the interior space of body 1305. This allows for the sterilization of the body member positioned within the interior space of body 1305.

By utilizing the apparatus and method described herein, the sterilization of the target area may be performed in the most convenient location, without causing any delay in the procedure once the patient enters into the room or suite where the procedure is to be performed. Additionally, the target area is protected from inadvertent contamination during the process of transporting the patient to the room or suite where the procedure is to be performed.

From the foregoing description, it should be appreciated that apparatus and methods for providing enhanced sterilization of target areas prior to surgical procedures is provided and presents significant benefits that would be apparent to one skilled in the art. Furthermore, while multiple embodiments have been presented in the foregoing description, it should be appreciated that a vast number of variations in the embodiments exist. Lastly, it should be appreciated that these embodiments are preferred exemplary embodiments only and are not intended to limit the scope, applicability, or configuration of the invention in any way. Rather, the foregoing detailed description provides those skilled in the art with a convenient road map for implementing a preferred exemplary embodiment of the invention, it being understood that various changes may be made in the function and arrangement of elements described in the exemplary preferred embodiment without departing from the spirit and scope of the invention as set forth in the appended claims.

The invention claimed is:

1. An apparatus comprising:
   an outer bag, said outer bag comprising an interior surface and an exterior surface;
   an inner bag, said inner bag comprising an interior surface and an exterior surface, said inner bag being generally contained within said outer bag;
   a delivery mechanism selectively configured to deliver at least one sterile substance to an interior space within said inner bag, said at least one sterile substance being selected from a group consisting of an aseptic and a disinfectant; and
   an aerating mechanism, said aerating mechanism being selectively configured to allow a mixture of an amount of the at least one sterile substance and an amount of air to pass through said aerating mechanism;
   said aerating mechanism being configured to convert said mixture of the at least one sterile substance and air into a foam; said foam being selectively configured to disinfect a target area of a patient's body.

2. The apparatus of claim 1 wherein said inner bag further comprises:
   said interior space comprising said interior surface and an annular space, wherein said outer bag further comprises an annular space and an interior space, said interior space of said outer bag comprising said interior surface of said outer bag and said annular space of said outer bag; wherein said interior space of said inner bag, said exterior surface of said inner bag, and said interior space of said outer bag are selectively configured to be sterile; wherein said inner bag and said outer bag are substantially constructed from at least one of the elements selected from a group consisting of plastic, transparent material, translucent material, substantially-transparent material, and substantially-translucent material.

3. The apparatus of claim 2 wherein said inner bag is generally disposed within said interior space of said outer bag and wherein said at least one sterile substance is generally disposed within said interior space of said inner bag.

4. The apparatus of claim 2 wherein said inner bag is disposed within said interior space of said outer bag, said outer bag being selectively configured to be detachably coupled to said inner bag.

5. The apparatus of claim 2 wherein said inner bag and said outer bag are selectively configured with a plurality of selectively removable and selectively positionable fasteners, wherein at least one body-fastener is selectively configured to detachably affix said inner bag to a contact-portion of said patient's body, wherein said contact-portion abuts the target area of said patient's body, wherein said target area is a surface area of said patient's body, wherein at least one bag-fastener is selectively configured to detachably affix said outer bag to said inner bag, wherein at least one clasping-fastener is selectively configured to be attached to said exterior surface of said outer bag and to be selectively clasped by a user of said apparatus.

6. The apparatus of claim 5 wherein said inner bag further comprises a hem and a body-fastener, said hem extending beyond a cuff-portion of said outer bag, said hem being folded back over an extended-portion of said outer bag and forming a cuff, said cuff being generally U-shaped, said cuff partially surrounding said extended-portion of said outer bag, wherein said body-fastener is selectively configured to detachably adhere said cuff to said contact-portion of said patient's body, said contact-portion of said patient's body abutting said target area of said patient's body, said contact-portion not coextensive with said target area of said patient's body.

7. The apparatus of claim 2 wherein said inner bag is selectively configured to be generally disposed within said interior space of said outer bag, wherein said inner bag is selectively configured to be selectively attached to said outer bag, said outer bag being selectively configured to be selectively detached from said inner bag.

8. The apparatus of claim 1 wherein:
said inner bag further comprises an annular space and an interior space, said interior space comprising said annular space and said interior surface;
said outer bag further comprises an interior surface, an annular space and an interior space, said interior space comprising said annular space and said interior surface; and
wherein said interior space of said inner bag, said exterior surface of said inner bag, and said interior space of said outer bag are selectively configured to be sterile;
wherein said inner bag and said outer bag are substantially constructed from at least one of the elements of a group consisting of plastic, transparent material, translucent material, substantially-transparent material, and substantially-translucent material;
said inner bag being disposed within said interior space of said outer bag, said at least one sterile substance being disposed within said interior space of said inner bag;
said outer bag being selectively configured to be detachably coupled with said inner bag;
said inner bag and said outer bag being selectively configured with a plurality of selectively removable, selectively positionable, and selectively repositionable fasteners, wherein said fasteners comprises at least one body-fastener, at least one bag-fastener, and at least one clasp-fastener;
wherein said at least one body-fastener is selectively configured to detachably affix said inner bag to a contact-portion of said patient's body, wherein said at least one bag-fastener is selectively configured to detachably affix said outer bag to said inner bag, wherein said at least one clasp-fastener is selectively configured to be selectively attached to said exterior surface of said outer bag and to be selectively clasped by a user of said apparatus.

9. The apparatus of claim 1 further comprising at least one pump, said at least one pump being selectively configured to pump at least one element selected from a group consisting of disinfectants, antiseptics, air, gases, vapors, mists, liquids, fluids, moistures, foams, gels, nanoparticles, particles, molecules, negative pressure, positive pressure, ambient pressure, equilibrium pressure, dynamic pressure, vapor pressure, stagnation pressure, surface pressure, and combinations thereof into said least one interior surface selected from the group consisting of said interior surface of said inner bag and said interior surface of said outer bag.

10. The apparatus of claim 9, further comprising at least one coupling mechanism, said at least one coupling mechanism being selectively configured to connect said at least one pump with at least one element selected from the group consisting of said interior space of said inner bag and said interior space of said outer bag; wherein said at least one coupling mechanism is at least one length of tubing, wherein said at least one length of tubing is selectively configured to transport at least one substance, said at least one substance being selected from a group consisting of disinfectants, antiseptics, air, gases, vapors, mists, liquids, fluids, moistures, foams, gels, nanoparticles, particles, molecules; wherein said at least one length of tubing is selectively configured to be coupled to at least one valve, wherein said at least one valve is selectively configured to be adjustable to regulate a flow of said at least one substance through said at least one length of tubing, said at least one substance selected from the group consisting of disinfectants, antiseptics, air, gases, vapors, mists, liquids, fluids, moistures, foams, gels, nanoparticles, particles, and molecules, negative pressure, positive pressure, ambient pressure, equilibrium pressure, dynamic pressure, vapor pressure, stagnation pressure, surface pressure, and combinations thereof.

11. An apparatus comprising:
an inner bag, said inner bag comprising an interior surface, an annular space, an exterior surface, and an interior space, said interior space comprising said annular space and said interior surface;
an outer bag, said outer bag comprising an interior surface, an annular space, an exterior surface, and an interior space, said interior space comprising said annular space and said interior surface;
a delivery mechanism selectively configured to deliver at least one sterile substance selected from a group consisting of an aseptic and a disinfectant;
at least one pump, said at least one pump being selectively configured to introduce into and suck from said interior surface of said inner bag at least one element selected from the group consisting of disinfectants, antiseptics, air, gases, vapors, mists, liquids, fluids, moistures, foams, gels, nanoparticles, particles, molecules, pressure, negative pressure, positive pressure, ambient pressure, equilibrium pressure, dynamic pressure, vapor pressure, stagnation pressure, surface pressure, and combinations thereof;
at least one aerating mechanism being selectively configured to allow a mixture of the at least one sterile substance and air to pass through said at least one aerating mechanism;
said at least one aerating mechanism configured to convert said mixture of the at least one sterile substance and air into a foam; said foam being selectively configured to disinfect a target area of a patient's body, at least one coupling mechanism being selectively configured to connect said at least one pump with at least one element selected from the group consisting of said interior space of said inner bag and said interior space of said outer bag; wherein said at least one coupling mechanism is at least one length of tubing, wherein said at least one length of tubing is selectively configured to transport at least one substance, said at least one substance being selected from the group consisting of aseptics, disinfectants, air, gases, vapors, mists, liquids, fluids, moistures, foams, gels, particles, molecules, nanoparticles, pressure, negative pressure, positive pressure, ambient pressure, equilibrium pressure, dynamic pressure, vapor pressure, stagnation pressure, and surface pressure, and combinations thereof; wherein said at least one aerating mechanism is selectively configured to be coupled to one or more ends of said at least one length of tubing; and
at least one valve, wherein said at least one valve is selectively configured to be coupled with said at least one length of tubing, wherein said at least one valve is selectively configured to be adjustable to regulate a flow of said at least one substance through said at least one length of tubing.

12. The apparatus of claim 11 further comprising at least one flow port, said at least one flow port connecting said at least one pump with at least one of the elements selected from the group consisting of said interior space of said inner bag and said interior space of said outer bag.

13. The apparatus of claim 12, wherein said at least one flow port is selectively configured to abut a cuff and a contact-portion of said patient's body, wherein said inner bag is selectively configured with at least one zip-lock open-closing device; wherein said inner bag is selectively configured to be coupled to at least one container, said at least one container is selectively configured to hang from an IV stand, said at least one sterile substance being disposed inside an interior space of said at least one container.

* * * * *